United States Patent [19]

Ackerman et al.

[11] Patent Number: 5,084,462

[45] Date of Patent: Jan. 28, 1992

[54] 4-QUINOLINE CARBOXYLIC ACID DERIVATIVES USEFUL AS IMMUNOSUPPRESSIVE AGENTS

[75] Inventors: Neil R. Ackerman, Greenville; Bruce D. Jaffee, Wilmington; Scott E. Loveless, Newark, all of Del.; Russell H. Neubauer, West Chester, Pa.

[73] Assignee: The Du Pont Merck Pharmaceutical Company, Wilmington, Del.

[21] Appl. No.: 545,048

[22] Filed: Jun. 28, 1990

Related U.S. Application Data

[62] Division of Ser. No. 186,243, Apr. 26, 1988, Pat. No. 4,968,701.

[51] Int. Cl.[5] .................. A61K 31/47; A61K 31/40

[52] U.S. Cl. .................. 514/311; 514/312; 514/314; 514/420

[58] Field of Search ............... 514/311, 312, 420, 314

Primary Examiner—Frederick E. Waddell
Assistant Examiner—Zohreh A. Fay

[57] ABSTRACT

4-Quinolinecarboxylic acids and derivatives thereof, such as 2-(2'-fluoro-1,1'-biphenyl-4-yl)-6-fluoro-3-methyl-4-quinolinecarboxylic acid, are useful as immunodulatory and anti-inflammatory agents. Pharmaceutical formulations containing such compounds are useful for the treatment of autoimmune diseases, organ transplantation rejection, graft vs. host disease, multiple sclerosis, and chronic inflammatory diseases such as rheumatoid arthritis.

3 Claims, No Drawings

4-QUINOLINE CARBOXYLIC ACID DERIVATIVES USEFUL AS IMMUNOSUPPRESSIVE AGENTS

This application is a division of Ser. No. 07/186,243 filed on Apr. 26, 1988, now U.S. Pat. No. 4,968,701.

BACKGROUND OF THE INVENTION

This invention relates to methods of treating immunological and inflammatory diseases and more particularly to methods of treating such diseases with 4-quinoline carboxylic acids and derivatives thereof.

U.S. Pat. No. 4,680,299, granted July 14, 1987, to Hesson describes phenylquinoline carboxylic acids and their derivatives as tumor inhibiting agents.

It has now been found that the compounds described in U.S. Pat. No. 4,680,299 are useful as immunomodulatory and antiinflammatory agents.

SUMMARY OF THE INVENTION

According to the present invention there is provided a method of treating an autoimmune disease in a mammal comprising administering to the mammal an immunosuppressive amount of a compound having the formula:

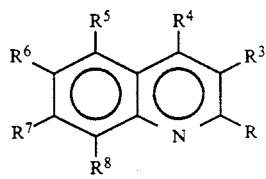

wherein
R is

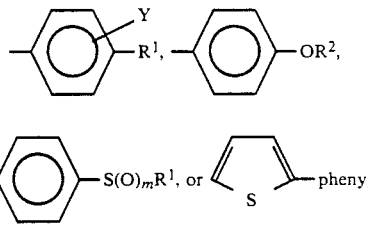

$R^1$ is $CH_3CH_2(CH_3)CH$, alkyl of 5-12 carbon atoms, cyclohexyl,

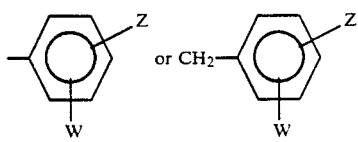

when R is

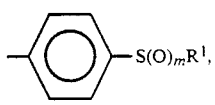

$R^1$ can be in addition alkyl of 3-4 carbon atoms; $R^2$ is

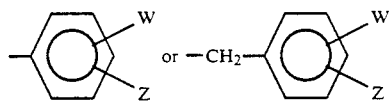

$R^3$ is H, alkoxy of 1-3 carbon atoms, or alkyl of 1-2 carbon atoms;

$R^4$ is $CO_2H$ or $CO_2R^{11}$;

$R^5$, $R^6$, $R^7$ and $R^8$ are independently H, F, Cl, Br, I, $CH_3$, $CF_3$, $SCH_3$ or $CH_2CH_3$, at least two of $R^5$, $R^6$, $R^7$ and $R^8$ being H;

$R^9$ and $R^{9A}$ are independently H or alkyl of 1 to 3 carbon atoms;

$R^{11}$ is $(CH_2)_{2-4}NR^9R^{9A}$;

W, Y and Z are independently H, F, Cl, Br, alkyl of 1-5 carbon atoms, $NO_2$, OH, $CF_3$ or $OCH_3$; m is 0 or 1; or a pharmaceutically suitable salt thereof;

with the following provisos:

(1) $R^5$, $R^6$ and $R^7$ cannot all be H;

(2) when $R^4$ is $CO_2CH_2CH_2N(CH_3)_2$, $R^6$ is $CH_2CH_3$, or $R^7$ is Cl, $R^1$ cannot be cyclohexyl;

(3) when $R^1$ is cyclohexyl and $R^3$ is H, $R^6$ must be Cl or F, but $R^6$ and $R^8$ cannot both be Cl; and (4) when $R^6$ is $CH^3$, then $R^7$ cannot be Cl.

Additionally provided is the above-described method wherein the compound is administered in combination with a nonsteroidal antiinflammatory drug.

PREFERRED EMBODIMENTS

Preferred compounds useful in the method have the formula:

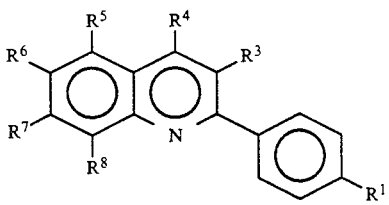

wherein
$R^1$ is cyclohexyl; phenyl; phenyl substituted with one halogen; alkyl of 1-5 carbon atoms or $CF_3$; phenoxy; or phenoxy substituted with one halogen or alkyl of 1-5 carbon atoms;

$R^3$ is H or alkyl of 1-2 carbon atoms;

$R^4$ is $CO_2H$, a sodium or potassium salt thereof; or $CO^2R^{11}$;

$R^5$ and $R^6$ are independently H, halogen, $CH_3$ or $CF_3$; $R^7$ and $R^8$ are independently H or halogen;

$R^{11}$ is $(CH_2)_{2-4}NR^9R^{9A}$; and $R^9$ and $R^{9A}$ are independently alkyl of 1 to 3 carbon atoms, or a pharmaceutically suitable salt thereof;

provided that $R^5$, $R^6$ and $R^7$ cannot all be H and that when $R^1$ is cyclohexyl and $R^3$ is H, $R^6$ must be Cl or F, but $R^6$ and $R^8$ cannot both be Cl, and when $R^6$ is $CH_3$, then $R^7$ cannot be Cl.

More preferred compounds useful in this invention have the formula:

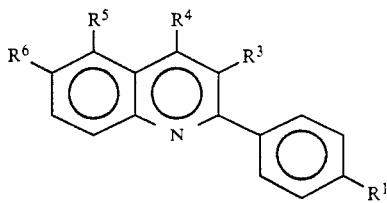

(III)

wherein

R$^1$ is cyclohexyl,

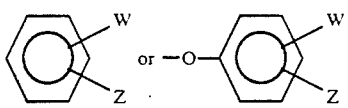

R$^3$ is H or alkyl of 1–2 carbon atoms;
R$^4$ is CO$_2$H, a sodium or potassium salt thereof, or CO$_2$R$^{11}$;
R$^5$ and R$^6$ are independently H, halogen or CF$_3$ provided that both R$^5$ and R$^6$ are not hydrogen;
R$^{11}$ is (CH$_2$)$_{2-4}$NR$^9$R$^{9A}$; and
R$^9$ and R$^{9A}$ are independently alkyl of 1 to 3 carbon atoms, and
W and Z are independently H, halogen, alkyl of 1–5 carbon atoms or CF$_3$;
provided that when R$^1$ is phenyl or phenoxy, and R$^5$ is H, then R$^6$ cannot be Br; and that when R$^1$ is cyclohexyl and R$^3$ is H, R$^6$ must be Cl or F.

Specifically preferred compounds useful in this invention are:

(1) 2-(1,1'-biphenyl-4-yl)-5-chloro-3-methyl-4-quinoline carboxylic acid, sodium or potassium salt
(2) 2-(1,1'-biphenyl-4-yl)-6-fluoro-3-methyl-4-quinoline carboxylic acid, sodium or potassium salt
(3) 6-fluoro-3-methyl-2-(4-phenoxyphenyl)-4-quinoline carboxylic acid, sodium or potassium salt
(4) 2-(4'-bromo-1,1'-biphenyl-4-yl)-6-fluoro-3-methyl-4-quinoline carboxylic acid, sodium or potassium salt
(5) 2-(2'-fluoro-1,1'-biphenyl-4-yl)-6-fluoro-3-methyl-4-quinoline carboxylic acid, sodium or potassium salt.

DETAILED DESCRIPTION OF THE INVENTION

The compounds useful in this invention are described in and prepared by methods set forth in U.S. Pat. No. 4,680,299, the disclosure, synthesis, and synthesis examples of which are hereby incorporated by reference.

The invention can be further understood by the following examples in which parts and percentages are by weight unless otherwise indicated; all temperatures are in degrees centigrade.

EXAMPLE 1

Part A:

2-(1,1'-Biphenyl-4-yl)-5-chloro-3-methyl-quinoline-4-carboxylic acid

A mixture of 4-chloroisatin (7.28 g, 0.04 mol), [*J. Am. Chem. Soc.*, 1251 (1956)], 4-phenylpropiophenone (8.8 g, 0.04 mol), diethylamine (4 ml, 0.04 mol) and ethanol (200 ml) was stirred for a period of 18 hours at room temperature. The precipitated solids were collected by filtration, washed with ice-cold ethanol and air dried to yield the adduct (9.1 g, 58%) m.p. 209°–214° dec.

Part B:

The above described adduct (9.1 g) was added to a mixture of tetrahydrofuran (200 ml), and concentrated HCl (200 ml) and heated at reflux for 24 hr. The reaction mixture was cooled, water (300 ml) was added and most of the tetrahydrofuran removed by evaporation in vacuo. The aqueous residue was cooled and the sticky solids collected by filtration. Trituration in 150 ml of boiling methanol yielded (4.8 g, 55%) m.p. 295°–297° dec.

C$_{23}$H$_{16}$ClNO$_2$ HRMS: 373.0869 Calcd, measured m/e 373.0814.

$^1$H NMR (DMSO-d$_6$):δ8.5(m,1H), 7.7–7.95(m,7H), 7.35–7.55(m,4H), 2.45(s,3H).

Part C: Sodium 2-(1,1'-Biphenyl-4-yl)-5-chloro-3-methyl-quinoline-4-carboxylate

To a suspension of the above acid (3.7 g, 0.01 mol) in ethanol 100 ml, sodium hydroxide (1N, 10 ml, 0.01 mol) was added, and gently warmed. The clear solution was then filtered and evaporated to dryness to yield (4.0 g) m.p. 320°–330° dec.

EXAMPLE 2

Part A:

2-(2-Fluoro-1,1'-biphenyl-4-yl)-6-fluoro-3-methyl-4-quinoline carboxylic acid

5-Fluoroisatin (72.6 g, 0.44 mole) and 4-(2-fluorophenyl)propiophenone (100 g, 0.44 mole) were suspended in 720 ml of ethanol and stirred mechanically as a solution of KOH (147.8 g, 2.64 mole) in 300 ml of water was added dropwise over 15 minutes. The reaction mixture was heated at reflux for 12 hours, cooled and the ethanol evaporated under reduced pressure. The resulting solid was dissolved in water and washed with ethyl ether. The aqueous layer was cooled to 5° and acidified with glacial acetic acid. The resulting precipitate was filtered, washed 2 times with 300 ml of ethyl ether and dried. Recrystallization from dimethylformamide and water gave 84 g of a white 2-(2'-Fluoro-1,1'-biphenyl-4-yl)-6-fluoro-3-methyl-4-quinoline carboxylic acid, m.p. 315°–317°.

Part B: Sodium 2-(2'-Fluoro-1,1'-biphenyl-4-yl)-6-fluoro-3-methyl-quinoline-4-carboxylate The compound of Part A (37.5 g, 0.10 mole) was suspended in 1,000 ml of ethanol and treated with 1N NaOH (100 ml, 0.10 mole). The mixture was warmed and stirred until clear; the ethanol and water were evaporated at reduced pressure to give 39.6 g of the white solid sodium 2-(2'-fluoro-1,1'-bipenyl-4-yl)6-fluoro-3-methylquinoline-4 -carboxylate, m.p. >360°.

Following the procedures of Examples 1 and 2 or the synthesis procedures described in U.S. Pat. No. 4,680,299, the compounds set forth in Table 1 were prepared.

TABLE 1

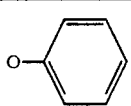

| Ex. No. | R¹ | R² | R³ | R⁴ | m.p. (°) |
|---|---|---|---|---|---|
| 3 | F | Na | $CH_3$ | 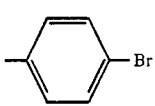 | >350 |
| 4 | F | Na | $CH_3$ | 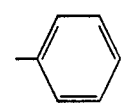 | >350 |
| 5 | $CH_3$ | Na | $CH_3$ | 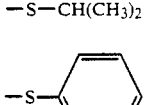 | >350 |
| 6 | F | Na | $CH_3$ | $-S-CH(CH_3)_2$ | 339-343 |
| 7 | Cl | Na | $CH_3$ | 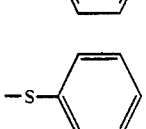 | 319-324 |
| 8 | Cl | K | $CH_3$ | 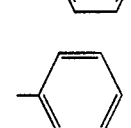 | 310-325 |
| 9 | F | Na | H | 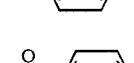 | >360 |
| 10 | F | Na | $CH_3$ | 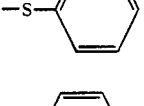 | 251-260 |
| 11 | F | Na | $OCH_3$ | 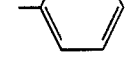 | 345-349 |
| 12 | Cl | Na | $CH_3$ | 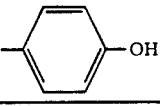 | >360 |

Utility

Results of the biological tests described below establish that the compounds useful in this invention have the ability to suppress/inhibit: the contact sensitivity response to 2,4-dinitrofluorobenzene (DNFB) in mice, the human mixed lymphocyte reaction, and adjuvant-induced arthritis in rats.

Contact sensitivity to DNFB has been extensively studied and characterized in the mouse to determine the regulatory mechanisms involved in cell mediated immune responses (Claman, et al., Immunol Rev 50:105, 1980). This is an antigen-specific T-cell mediated inflammatory response that represents delayed-type hypersensitivity reactions seen in both humans and other mammals. The primary use of the human mixed lymphocyte reaction is for the determination of transplantation compatibility between the donor (graft) and the recipient (Park and Good, p. 71. In Yunis, et al., Tissue typing and organ transplantation. 1973 Academic Press Inc., N.Y.).

Rat adjuvant-induced arthritis represents a systemic inflammatory disease with bone and cartilage changes similar to that observed in rheumatoid arthritis, but in an accelerated time span (Pearson, Arth Rheum 7:80, 1964).

Most clinically effective drugs exhibit activity in these biological tests similar to that observed with the compounds useful in this invention (Fenichel and Chirigos, ed, Immune Modulation Agents and Their Mechanisms, Dekker, Inc., N.Y. 1984.

Contact Sensitivity Response to ENFB in Mice

Balb/c female mice ($\simeq$20g, Charles River) were sensitized on the shaved abdomen with 25 μl of 0.5% 2,4-dinitrofluorobenzene (ENFB, Eastman Kodak Co.) in a vehicle of 4:1 acetone:olive oil on days 0 and 1. Mice were ear challenged with 20 μl of 0.2% DNFB in a vehicle of 4:1 acetone:olive oil on day 5. A constant area of the ears was measured immediately before challenge and 24 hours later with an engineer's micrometer. Ear swelling was expressed as the difference in ear thickness before and after challenge in units of $10^{-4}$ inches±SEM. Percent suppression was calculated as:

$$\% \text{ Suppression} = 1 - \frac{\text{compound treated} - \text{negative control}}{\text{positive control} - \text{negative control}} \times 100$$

Compounds were administered orally from days—2 through day 6 and were prepared in 0.25% Methocel ® (Dow Chemical Co.). Control animals received only vehicle (0.25%) Methocel ®). Negative controls were not sensitized on days 0 and 1 but were ear challenged on day 5. Ten mice were used per group. Results with compounds of invention and drugs used clinically are shown in Tables 2 and 3.

TABLE 2

| Treatment | Dose (mg/kg) | Ear Swelling[a] (units ± SEM) | % Suppression | $ED_{50}$ |
|---|---|---|---|---|
| Negative | Vehicle | 0.74 ± 0.52 | — | — |
| Positive | Vehicle | 74.11 ± 3.78 | 0 | — |
| Dexamethasone | 0.2 | 52.95 ± 3.39 | 28.84 | 1.50 |
| | 1.0 | 41.60 ± 2.46 | 44.31 | |
| | 5.0 | 23.79 ± 2.71 | 68.58 | |
| | 10.0 | 15.50 ± 2.10 | 79.88 | |
| Cyclosporin A | 2.0 | 56.15 ± 3.74 | 24.48 | 70.00 |
| | 10.0 | 66.58 ± 3.75 | 10.27 | |
| | 50.0 | 47.90 ± 3.76 | 35.72 | |
| | 100.0 | 7.80 ± 2.04 | 90.37 | |
| Methotrexate | 0.4 | 71.30 ± 2.96 | 3.83 | 9.00 |
| | 2.0 | 60.80 ± 1.99 | 18.14 | |
| | 10.0 | 36.10 ± 3.23 | 51.80 | |
| | 20.0 | 27.45 ± 4.99 | 63.59 | |
| Example 1 | 0.4 | 66.05 ± 4.32 | 10.99 | 3.50 |
| | 2.0 | 56.94 ± 4.80 | 23.40 | |
| | 10.0 | 6.10 ± 0.75 | 92.69 | |
| | 20.0 | 5.20 ± 1.17 | 93.92 | |
| Example 2 | 0.4 | 51.95 ± 2.33 | 30.20 | 0.95 |
| | 2.0 | 25.61 ± 3.39 | 66.10 | |
| | 10.0 | 6.40 ± 1.09 | 92.28 | |

TABLE 2-continued

| Treatment | Dose (mg/kg) | Ear Swelling[a] (units ± SEM) | % Suppression | ED$_{50}$ |
|---|---|---|---|---|
| | 20.0 | 4.75 ± 1.20 | 94.53 | |

[a]Increase in ear thickness from day 5 to day 6, unit = $10^{-4}$ inches

TABLE 3

| Treatment | Dose (mg/kg) | Ear Swelling[a] (units ± SEM) | % Suppression |
|---|---|---|---|
| Negative | Vehicle | 2.60 ± 0.73 | — |
| Positive | Vehicle | 73.11 ± 3.69 | 0 |
| Dexamethasone | 1.0 | 42.20 ± 2.61 | 43.83 |
| Cyclosporin A | 20.0 | 74.30 ± 2.86 | −1.69 |
| Methotrexate | 20.0 | 16.94 ± 2.10 | 79.66 |
| Example 3 | 20.0 | 14.25 ± 1.49 | 83.48 |
| Example 4 | 20.0 | 11.80 ± 1.03 | 86.95 |
| Example 5 | 20.0 | 35.47 ± 2.31 | 53.37 |
| Example 6 | 20.0 | 58.20 ± 4.63 | 21.14 |
| Example 7 | 20.0 | 62.95 ± 3.40 | 14.40 |
| Example 8 | 20.0 | 63.25 ± 3.58 | 13.98 |
| Example 9 | 20.0 | 42.60 ± 2.68 | 43.27 |
| Example 10 | 20.0 | 57.28 ± 2.36 | 22.45 |
| Example 11 | 20.0 | 20.85 ± 2.53 | 74.12 |
| Example 12 | 20.0 | 54.58 ± 3.21 | 26.28 |

[a]increase in ear thickness from day 5 to day 6, unit = $10^{-4}$

Human Mixed Lymphocyte Reaction

Blood was obtained by venipuncture from two non-related human donors. Peripheral blood mononuclear cells (PBMC) were isolated from these samples by using the Leuco Prep procedure (Becton-Dickinson). PBMC were washed twice in phosphate buffered saline (without calcium and magnesium) and the separate cell isolations were adjusted to the appropriate concentrations in media (RPMI 1640) supplemented with 10% human AB serum and 50 μl/ml gentamicin. Cells from donor A ($2 \times 10^5$) were incubated with cells from donor B ($2 \times 10^5$) in 96 well round bottom microliter plates at 37° C., 5% $CO_2$ for 6 days. Eighteen hours prior to harvesting cells from the plates, all wells were pulsed with 1 μCi of $^3$H-thymidine. Cells from the plates were harvested on day 6 and $^3$H-thymidine incorporation was determined using a scintillation counter. Test results are shown in Table 4.

TABLE 4

| Compound | IC$_{50}$ (M) |
|---|---|
| Indomethacin | $>10^{-6}$ |
| Cyclosporin A | $1.6 \times 10^{-8}$ |
| Methotrexate | $2.5 \times 10^{-9}$ |
| Example 1 | $9.6 \times 10^{-9}$ |
| Example 2 | $2.5 \times 10^{-8}$ |

Adjuvant-Induced Arthritis

Male Lewis rats (Charles River) weighing 160-210 grams were injected subcutaneously with 0.1 ml of Freund's Complete Adjuvant containing 5 mg of M. butyricum/ml of paraffin oil (Difco Laboratories) into the plantar region of the right hind paw. Paraffin oil was injected for non-arthritic controls. Ten rats were used per group. Compounds were prepared in 0.25% Methocel® (Dow Chemical Co) with one drop of Tween® 80 per 10 ml of Methocel®. Animals were dosed every day beginning on the day of paw injection until day 18. The weight of each animal was recorded every other day beginning on the day of the paw injections. On day 18 the animals were weighed, and the non-injected hind paw volume was measured using a Ugo Basile Volume Differential Plethysmometer. The results are shown in Table 5.

TABLE 5

| Group (AA) | Compound (mg/kg) | Weight Gain (g) | Non-Injected Hind-Paw Volume (ml) | % Suppression |
|---|---|---|---|---|
| A− | Vehicle | 85.6 ± 4.8 | 1.12 ± 0.01 | — |
| B+ | Vehicle | −20.3 ± 2.9 | 1.88 ± 0.05 | — |
| C+ | Example 1 (10.00) | −14.0 ± 4.2 | 1.87 ± 0.08 | 1.4 |
| D+ | Example 1 (17.5) | 2.8 ± 5.3 | 1.72 ± 0.08 | 20.8 |
| E+ | Example 1 (25.0) | 20.6 ± 6.3 | 1.34 ± 0.10 | 70.6 |
| F+ | Example 2 (2.0) | −1.5 ± 3.6 | 1.62 ± 0.05 | 34.5 |
| G+ | Example 2 (10.0) | 65.6 ± 5.2 | 1.15 ± 0.02 | 96.2 |
| H+ | Example 2* (25.0) | | | |

Example 1: ED$_{50}$ = 21 mg/kg
Example 2: ED$_{50}$ < 10 mg/kg
*Toxic by day 7

In summary, test results show that the compounds useful in this invention have both immunomodulating and anti-inflammatory effectiveness. Based on these data, the compounds useful in this invention should be efficacious in treating autoimmune diseases such as rheumatoid arthritis, systemic lupus erythematosus, multiple sclerosis, and myasthenia gravis; all of which involve T lymphocyte mediated components similar to those known in the contact sensitivity model. Activities in the human mixed lymphocyte reaction indicate that the compounds of invention should be effective in preventing organ transplantation rejection and graft vs. host disease. These compounds were also effective in the adjuvant-induced arthritis model and should therefore be useful anti-inflammatory agents for the treatment of chronic inflammatory diseases such as rheumatoid arthritis, psoriasis, and inflammatory bowel disease.

DOSAGE FORMS

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 0.1 to 400 milligrams per kilogram of body weight. Ordinarily 1 to 100, and preferably 10 to 50 milligrams per kilogram per day is effective to obtain desired results.

Dosage forms (compositions) suitable for internal administration contain from about 10-500 milligrams to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders or in liquid dosage forms, such as elixirs, syrups, and suspensions, it can also be administered parenterally, in sterile liquid dosage forms.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antiomidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

CAPSULES

A large number of unit capsules are prepared by filling standard two piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs. Suitable dosages, dosage forms and administration routes are illustrated in Table 6.

TABLE 6

| Examples of NSAID's that can be combined with the 4-quinolinecarboxylic acids used in this invention | | |
|---|---|---|
| Drug | Dose (mg) | Formulation Route |
| Indomethacin | 25 (⅔ times daily) | Tablet Oral |
| Meclofenamate | 50–100 (⅔ times daily) | Tablet Oral |
| Ibuprofen | 300–400 (⅔ times daily) | Tablet Oral |
| Piroxicam | 10–20 (¼ times daily) | Tablet Oral |
| Sulindac | 150–200 (2 times daily) | Tablet Oral |
| Azapropazone | 200–500 (⅔ times daily) | Tablet Oral |

What is claimed is:

1. A method of treating rheumatoid arthritis, systemic lupus erythematosus, multiple sclerosis, myasthenia gravis, graft versus host disease, organ transplantation rejection, or a chronic inflammatory disease in a mammal comprising administering to the mammal a therapeutically effective amount of nonsteroidal antiinflammatory drug in combination with a compound having the formula:

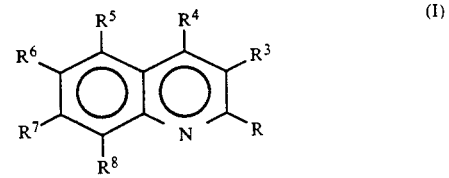

(I)

wherein:
R is

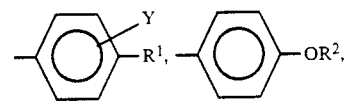

-continued

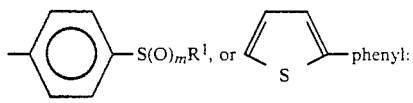

$R^1$ is $(CH_3CH_2)(CH_3)CH$, alkyl of 5–12 carbon atoms, cyclohexyl,

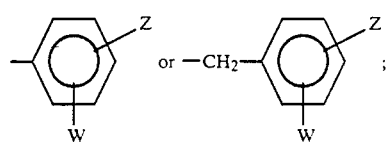

when R is

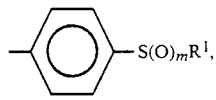

then $R^1$ can be in addition alkyl of 3–4 carbon atoms;

$R^2$ is

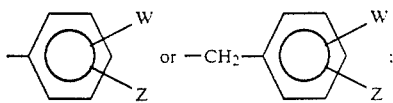

$R^3$ is H, alkoxy of 1–3 carbon atoms, or alkyl or 1–2 carbon atoms;

$R^4$ is $CO_2H$ or $CO_2R^{11}$;

$R^5$, $R^6$, $R^7$ and $R^8$ are independently H, F, Cl, Br, I, $CH_3$, $CF_3$, $SCH_3$, or $CH_2CH_3$, at least two of $R^5$, $R^6$, $R^7$ and $R^8$ being H;

$R^9$ and $R^{9A}$ are independently H or alkyl of 1 to 3 carbon atoms;

$R^{11}$ is $(CH_2)_{2-4}NR^9R^{9A}$;

W, Y and Z are independently H, F, Cl, Br, alkyl of 1–5 carbon atoms, $NO_2$, OH, $CF_3$ or $OCH_3$; and m is 0 or 1; or a pharmaceutically suitable salt thereof;

with the following provisos:
(1) $R^5$, $R^6$ and $R^7$ cannot all be H;
(2) when $R^4$ is $CO_2CH_2CH_2N(CH_3)_2$, $R^6$ is $CH_2CH_3$, or $R^7$ ic Cl, $R^1$ cannot be cyclohexyl;
(3) when $R^1$ is cyclohexyl and $R^3$ is H, $R^6$ must be Cl or F, but $R^6$ and $R^8$ cannot both be Cl; and
(4) when $R^6$ is $CH_3$, then $R^7$ cannot be Cl; and
(5) when $R^4$ is $CO_2H$, $R^1$ or $R^2$ is phenyl, and $R^5$, $R^7$, and $r^8$ are H, then $R^6$ cannot be Br.

2. The method of claim 1 wherein the compound is 2-(1,1'-biphenyl-4-yl)-5-chloro-3-methyl-4-quinoline carboxylic acid, sodium or potassium salt.

3. The method of claim 1 wherein the compound is 2-(2'-fluoro-1,1'-biphenyl-4-yl)-6-fluoro-3-methyl-4-quinoline carboxylic acid, sodium or potassium salt.

R

* * * * *